United States Patent [19]

McKinley

[11] Patent Number: 5,673,147
[45] Date of Patent: Sep. 30, 1997

[54] STEREO VIDEO ENDOSCOPE OBJECTIVE LENS SYSTEMS

[75] Inventor: Harry R. McKinley, Southampton, Mass.

[73] Assignee: McKinley Optics, Inc., Southampton, Mass.

[21] Appl. No.: 424,704

[22] Filed: Apr. 18, 1995

[51] Int. Cl.$^6$ .................................................. G02B 27/22
[52] U.S. Cl. ........................ 359/462; 359/376; 359/466; 359/475
[58] Field of Search ............................ 359/462, 466, 359/470, 473, 475–477, 643, 656, 661, 664, 376–378; 250/208.1

[56] References Cited

U.S. PATENT DOCUMENTS

| | | | |
|---|---|---|---|
| 3,655,259 | 4/1972 | Miyauchi et al. | 359/376 |
| 4,061,135 | 12/1977 | Widran et al. | 600/111 |
| 4,615,332 | 10/1986 | Buess et al. | 600/113 |
| 4,651,201 | 3/1987 | Schoolman | 348/45 |
| 4,710,000 | 12/1987 | Spitznas et al. | 350/516 |
| 4,862,873 | 9/1989 | Yajima et al. | 600/111 |
| 4,873,572 | 10/1989 | Miyazaki et al. | 348/45 |
| 4,895,431 | 1/1990 | Tsujiuchi et al. | 359/29 |
| 5,122,650 | 6/1992 | McKinley | 250/208.1 |
| 5,191,203 | 3/1993 | McKinley | 250/208.1 |
| 5,459,605 | 10/1995 | Kempf | 359/462 |

FOREIGN PATENT DOCUMENTS 0 211 783   7/1986   European Pat. Off. .

*Primary Examiner*—John D. Lee
*Attorney, Agent, or Firm*—Lappin & Kusmer LLP

[57] ABSTRACT

A stereoscopic objective lens system for video endoscopes and borescopes includes two full-diameter doublets and two identical half-diameter ball lenses. The full-diameter doublets collimate object points, imaging object points to infinity. The full-diameter doublets present equal-angle pairs from symmetrically disposed object points to the ball lenses. This equal-angle property enables accurate object/image mapping onto the final stereo image pair such that all parts of each left/right image can be mapped to within a fraction of a video pixel to each other.

12 Claims, 5 Drawing Sheets

STEREO VIDEO ENDOSCOPE OBJECTIVE LENS SYSTEMS

BACKGROUND OF THE INVENTION

This invention relates generally to optical lens systems, and, more particularly, relates to stereoscopic objective lens designs adapted for use in stereo video endoscopes.

Medical endoscopes are widely utilized to view internal regions of the human body during diagnostic, surgical, and other medical procedures. Endoscopes typically include a long, thin, rigid or semi-rigid optical cylinder affixed to a viewing mechanism. The cylinder is sufficiently narrow to be inserted through a small opening in the body, which may be natural or surgical. When the endoscope is inserted and positioned for use, an image of the object being viewed is formed at an inserted end of the endoscope by an objective lens. The image passes through a series of relay lenses down the cylinder to an eye lens or video camera at a viewing end of the endoscope.

In recent years, researchers have attempted to improve the imaging available through endoscopic devices by developing stereoscopic video endoscopes. These endoscopes present an apparently three-dimensional image on a video monitor. The stereoscopic effect is created by producing two optical images—a left image and a right image—through the endoscope. The left and right optical images are presented by the endoscope to left and right image sensors, which may be charge-coupled device (CCD) cameras or other image sensing devices. The sensing devices convert the left and right optical images into left and right video images which are then presented as alternating left/right images on a monitor, at a switching rate higher than the flicker-sensing limit of the human eye, so that observed images appear flicker-free.

The images are alternately switched from a left-hand polarization mode to a right-hand polarization mode, such that, for example, the left image has a left-hand polarization and the right image has a right-hand polarization. In accord with this example, the observer wears polarized glasses in which the left lens has the left-hand polarization and the right lens has the right-hand polarization. Thus, the left eye sees only images from the left channel of the endoscope system and the right eye sees only images from the right channel, resulting in stereoscopic viewing.

The following United States and foreign patents disclose examples of stereo endoscopes, some of which utilize video imaging and display elements:

U.S. Pat. No. 4,061,135
U.S. Pat. No. 4,615,332
U.S. Pat. No. 4,651,201
U.S. Pat. No. 4,862,873
U.S. Pat. No. 4,873,572
U.S. Pat. No. 4,895,431
U.S. Pat. No. 5,122,650
U.S. Pat. No. 5,191,203
EP Patent No. 211,783

In particular, U.S. Pat. No. 4,061,135 discloses a binocular endoscope in which images are transmitted from the viewed object to the viewing station through an optical system utilizing a dove prism and mechanical linkage to compensate for rotation effects.

U.S. Pat. No. 4,615,332 discloses a binocular endoscope having flexible light guides and binocular eyepieces.

U.S. Pat. No. 4,651,201 discloses a stereoscopic video endoscope including two image guides and an illumination light guide. The image guides are optically coupled to a stereoscopic viewer for three dimensional viewing. The viewer includes couplings for attaching miniature video camera that can be connected to a head mounted stereoscopic video display.

U.S. Pat. No. 4,862,873 discloses a stereo endoscope having two light guides for carrying images of an object an electro-optical imaging assembly. A lens system directs light from the object to the objective end of the light guides. Illuminating light is transmitted to the object from the opposite end of one light guide, thereby illuminating the object. Simultaneously, the image transmitted through the other optical guide is conducted to the imaging assembly.

U.S. Pat. No. 4,873,572 discloses a stereo endoscope having a CCD camera module and two image-forming lens systems that form two object images. The object images are integrated and directed to the CCD camera to provide a stereoscopic output. The lens systems include red, green, and blue color filters disposed at the camera imaging surface.

U.S. Pat. No. 4,895,431 discloses an endoscope apparatus that generates a three-dimensional image of an object from overlapping images recorded by a camera. The endoscope includes an insertion module and a movable end section capable of being deflected through an angle. A first image is recorded with the end section positioned at a first angle. A second image, partially overlapping the first image, is recorded after moving the end section to a second angle. The relative position of the movable end section is detected by an encoder that generates position signals for input to a microprocessor, which utilizes the position signals to generate a three-dimensional image of the object.

U.S. Pat. No. 5,122,650 discloses a stereo video endoscope objective lens system using six doublet lenses to generate pixel mapped left-right images for stereo viewing.

U.S. Pat. No. 5,191,203 discloses a stereo video endoscope objective lens system using lenses having a graded index of refraction to generate pixel mapped left-right images for stereo viewing.

European Patent No. 211,783 discloses a stereo video endoscope in which two light pipes deliver two images of the same object. These images are presented by a binocular device to the user's eyes to show a three dimensional image of the target. The apparatus includes two television cameras and video recorders for recording the images. The recorded images can be displayed on separate screens and viewed by a binocular viewing system.

Most conventional stereo endoscopes, however, share a number of deficiencies associated with their objective lens systems. These problems include a bulky and unwieldy configuration; high cost and complexity of fabricating the objective lens system; and the less than optimal optical performance afforded by conventional objective lens systems.

An additional problem associated with conventional stereo video endoscope objectives involves the requirement that all portions of each left/right image be mapped to within a fraction of a video pixel to each other. This pixel mapping condition is a significant optical design constraint, because the object-to-image ray paths through the lens system are quite different for the left and right image points associated with a common object point.

Accordingly, it is a general object of the present invention to provide improved stereo endoscope objective lens systems that overcome the problems associated with conventional designs.

A more specific object is to provide an improved stereo endoscope objective lens system having optical elements that facilitate assembly of the system.

It is another object of the invention to provide an improved stereo endoscope objective lens system having elements that are substantially less expensive to manufacture than the elements of conventional systems.

A further object is to provide an improved stereo endoscope objective lens system having optical performance characteristics that are substantially superior to the performance characteristics of conventional systems.

Another object of the invention is to provide a stereo objective lens system affording a pixel mapped image.

The above and other objects and advantages of this invention will become more readily apparent when the following description is read in conjunction with the accompanying drawings.

SUMMARY OF THE INVENTION

The foregoing objects are attained by the invention, which provides an improved stereo endoscope objective lens system for video imaging in medical endoscopes and industrial borescopes.

One aspect of the invention includes two full-diameter (D) doublets disposed along an optical axis, and a left/right stereo lens pair. The stereo lens pair includes a set of two spherical, or ball lenses, each having a cylindrical lateral surface with a circular cross-section having a diameter D/2. The full-diameter doublets substantially collimate object points, i.e., image them substantially to infinity. The stereo lens pair is disposed to collect light from the second doublet, with the optical axis of each ball lens being substantially parallel, and offset by D/4 from the optical axis of the doublets.

The doublets and the stereo lens pair cooperate so that the doublets present equal angle light ray pairs from symmetrically disposed object points to the ball lenses of the stereo lens pair. The left and right ball lenses generate left and right images respectively, at an image plane, where corresponding portions of those images are mapped to within a selected distance of each other.

In a further aspect of the invention, the ball lenses are particularly advantageous compared to the prior art, because they can be most economically fabricated in production quantities. This is advantageous because these small lenses are inherently difficult to manufacture.

In another aspect of the invention, the large collimator doublets provide accurate object/image mapping onto the final stereo image pair. In this design, the larger, and hence easier to fabricate doublets carry the corrective burden, so that the smaller, more difficult to manufacture lenses can be made a simple as possible.

The invention will next be described in connection with certain illustrated embodiments; however, it should be clear to those skilled in the art that various modifications, additions and subtractions can be made without departing from the spirit or scope of the claims.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWING

For a fuller understanding of the nature and objects of the invention, reference should be made to the following detailed description and the accompanying drawings, in which.

DESCRIPTION OF ILLUSTRATED EMBODIMENTS

Figure 1:
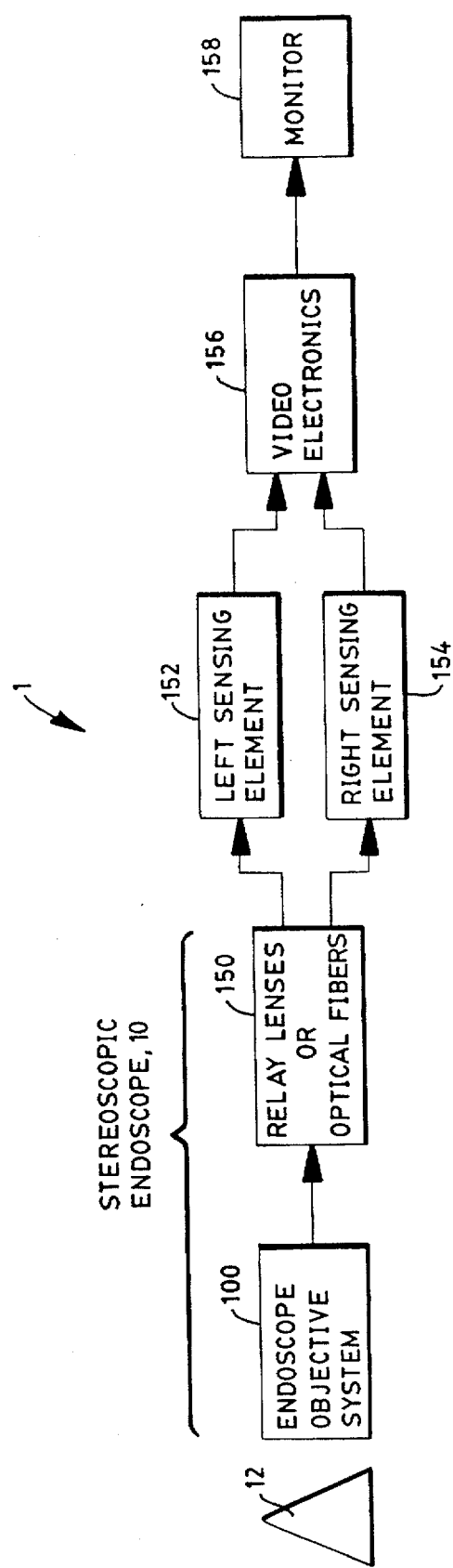
FIG. 1 is a schematic diagram depicting a stereo video endoscope utilizing an objective lens system constructed in accordance with the invention.

FIG. 1 depicts the invention, an endoscope objective system 100, utilized in a stereo video endoscopy system 1 for generating stereoscopic images of an object 12. The system 1 principally includes a stereoscopic endoscope 10 containing objective system 100; sensing modules 152, 154; switching module 156; and a monitor 158. In addition to objective lens system 100, the endoscope 10 includes conventional relay lenses or optical fibers 150 for transmitting light collected by the endoscope objective system 100 to light sensing modules 152, 154.

The endoscope objective system 100 generates left and right optical images of the object 12 that are processed by sensing elements 152, 154 and video switching module 156 in a known manner to display an apparently three-dimensional image of the object 12 on video monitor 158.

The stereoscopic effect is created by producing two optical images—a left image and a right image —through the endoscope objective system 100. The left and right optical images generated by the objective system 100 are presented by the relay lens or optical fiber system 150 to left and right image sensors 152, 154, which can be conventional charge-coupled device (CCD) cameras or other image sensing devices. The CCD elements operate in a known manner to convert the light collected by the objective system 100, and transmitted by the relay lenses or optical fibers 150, into electrical signals representative of the left and right optical images of the object 12.

Conventional video switching circuitry 156 transmits the electronic signals representative of left and right video images as alternating left-right images on the monitor 158. In accord with known video practice, these alternating images are presented at a switching rate higher than the flicker-sensing limit of the human eye, so that observed images appear flicker-free.

Moreover, the images can be alternately switched from a left-hand polarization mode to a right-hand polarization mode, such that, for example, the left image has a left-hand polarization and the right image has a right-hand polarization. The observer wears polarized glasses in which the left lens has the left-hand polarization and the right lens has the right-hand polarization. Thus, when the observer views the monitor 158, the left eye sees only images from the left channel of the endoscope system and the right eye sees only images from the right channel, resulting in stereoscopic viewing. Video switching and display equipment of this type is commercially available from Stereographics, Inc. of San Rafael, Calif.; and from Tektronix Corp., of Beaverton, Oreg.

The accuracy and quality of the image displayed on monitor 158 is controlled by the performance of the endoscope objective system 100, which is the subject of the present invention.

Figure 2:
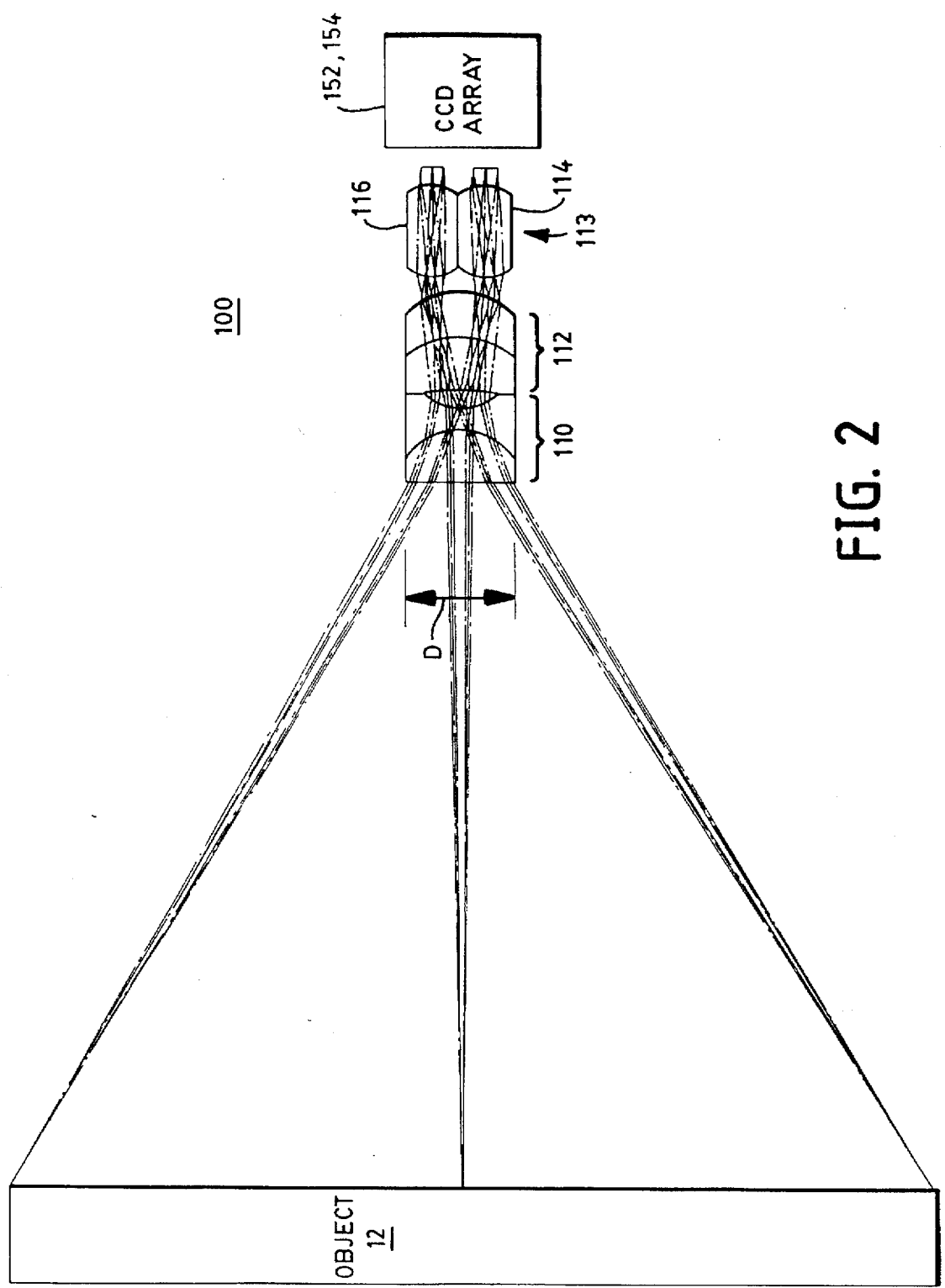
FIG. 2 is an optical schematic diagram depicting an objective lens system constructed in accordance with the invention, showing light rays transmitted through the system.
Figure 3:
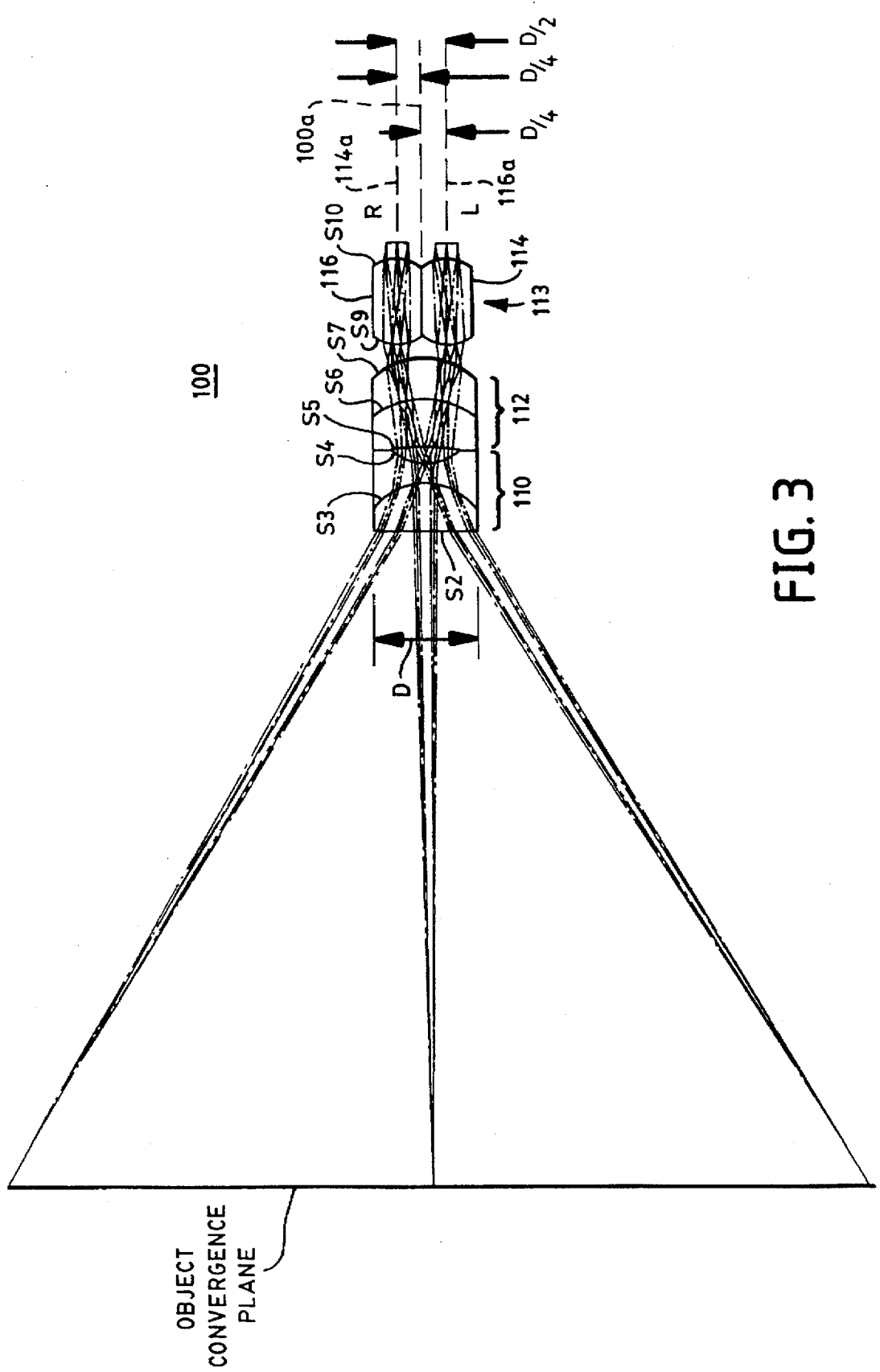
FIG. 3 is an optical schematic diagram depicting an objective lens system constructed in accordance with the invention, identifying optical surfaces.
Figure 4A:
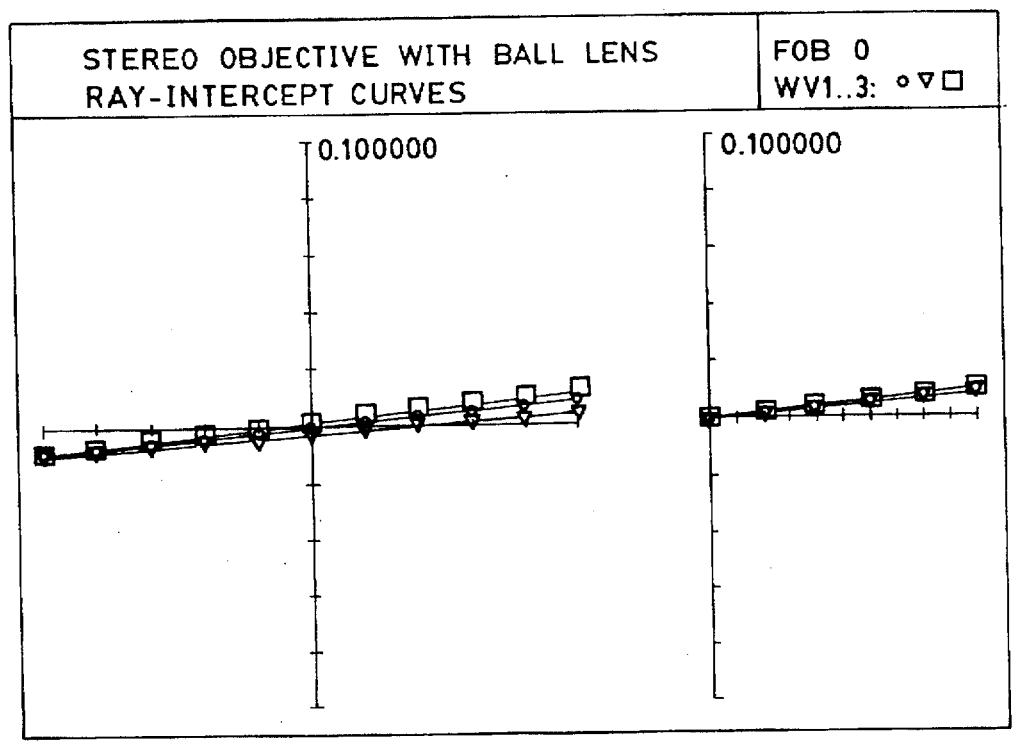
FIGS. 4A–4D show ray intercept and optical path difference curves the embodiment of FIGS. 2 and 3.
Figure 4B:
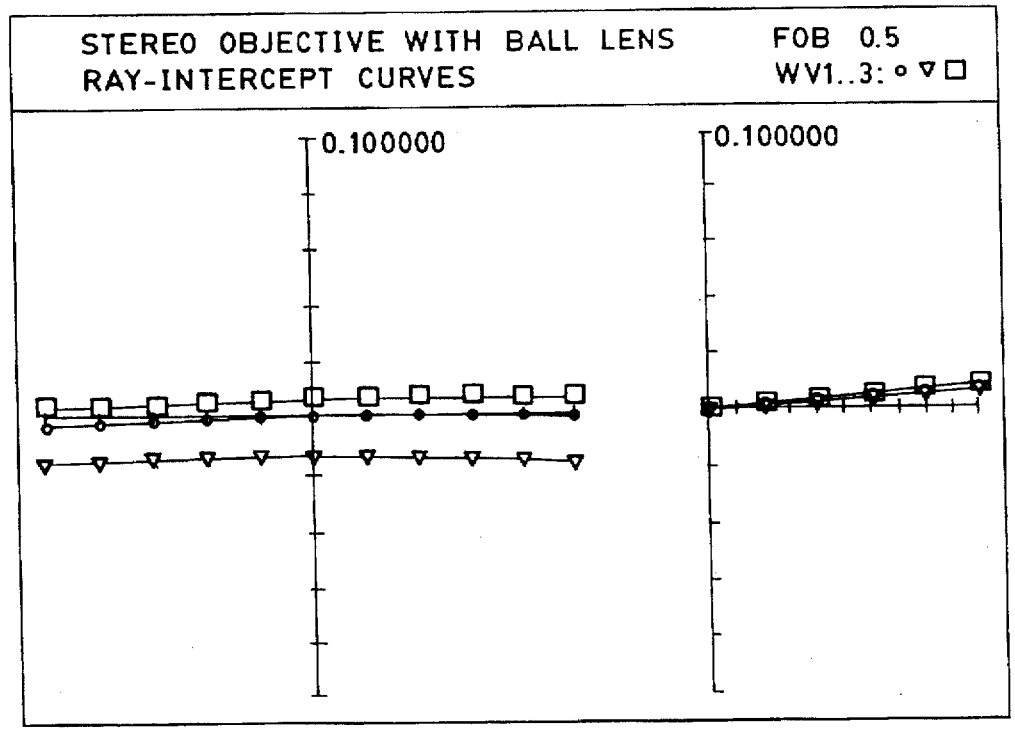
Figure 4C:
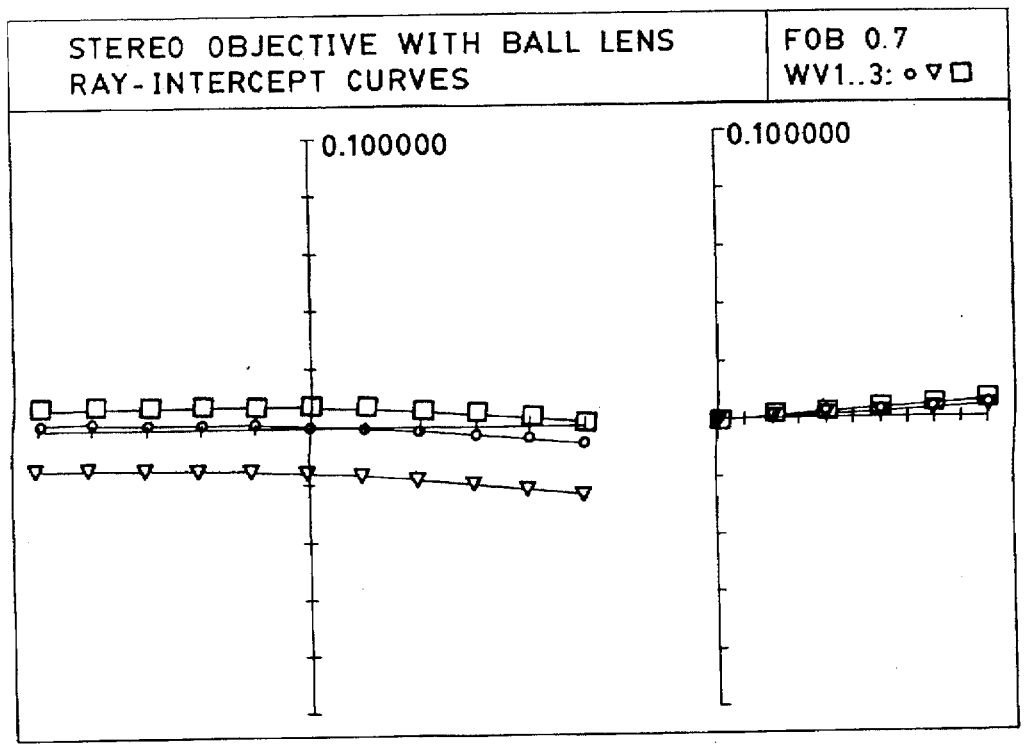
Figure 4D:
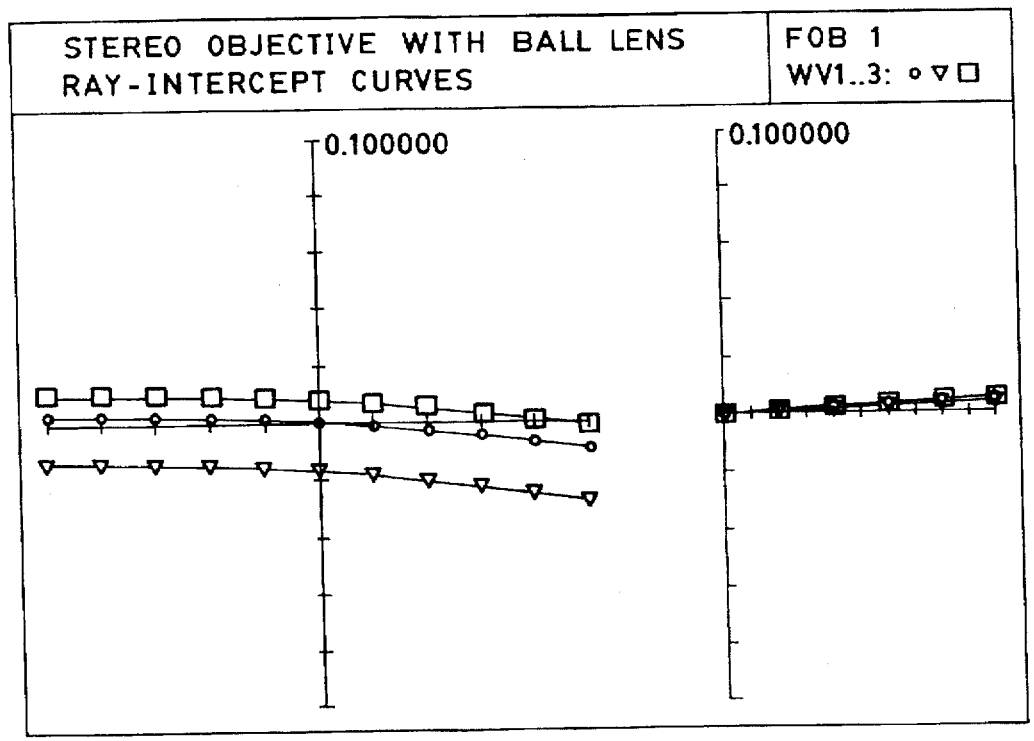

FIGS. 2 and 3 depict an objective lens system 100 constructed in accordance with the invention, showing light rays transmitted through the system.

The objective system 100 of FIGS. 2 and 3 include a first doublet 110 and a second doublet 112 positioned in sequence along and centered about a common system axis 100a, followed by a stereo lens set 113. Both doublets have circular cross sections with a diameter D. The lens set 113 includes a pair of matched, cylindrical side wall ball lenses 114, 116, each having a circular cross-section with diameter D/2, extending along an associated one of ball lens axes 114a and 116a which are parallel to, and spaced apart by D/2 from, the system axis 100a. The two doublets 112, 114 cooperate to collimate object points, i.e., image them to infinity.

Those skilled in the art will appreciate that the lenses of the objective system 100 depicted in FIGS. 2 and 3 define a sequence of 12 optical surfaces. A working example of a set of lenses for objective system 100 is set forth below in Table A. Reference numerals S2–S7, S9 and S10 shown in FIG. 3 correspond to numerals 2–7, 9 and 10 respectively in the "SURFACE" column of Table A. As those skilled in the an will appreciate, surfaces 1, 8, 11, and 12 do not correspond to physical surfaces and are indicated in Table A for convenience of analysis. FIG. 3 shows reference designations S2–S7, S9 and S10 overlaid onto the system of FIG. 2.

TABLE A

| SURFACE | RADIUS | THICKNESS | GLASS |
| --- | --- | --- | --- |
| 1 | — | –3.678088 | AIR |
| 2 | — | 3.000000 | SIO2 C |
| 3 | –3.650000 | 1.200000 | SF1 C |
| 4 | 3.101000 | 0.983255 | AIR |
| 5 | 15.121014 | 3.000000 | LAKN12 C |
| 6 | –5.000000 | 2.500000 | F4 C |
| 7 | –4.443995 | 1.400000 | AIR |
| 8 | — | 2.200000 | AIR |
| 9 | 2.500000 | 5.000000 | BK7 C |
| 10 | –2.500000 | 1.046744 | AIR |
| 11 | — | 0.001000 | BK7 C |
| 12 | — | — | AIR |

In Table A, the numerical values in the "RADIUS" and "THICKNESS" columns are set forth in millimeters. The "GLASS" descriptions are standard optical glass characterizations as found in the product catalog of the Schott Glass Company of Germany. The "THICKNESS" column refers to the distance to the next optical surface. The "RADIUS" column refers to the radii of curvature of the respective curved surfaces. For example, Table A describes lens 116 as a ball lens because surfaces 9 and 10 have 2.5, and –2.5 millimeter radii of curvature, respectively, and the distance between surfaces 9 and 10 is 5 millimeters. Lenses 114 and 116 are ball (or spherical) lenses that have been ground to have cylindrical lateral surfaces, with a circular cross-section (transverse to the respective axes 114A and 116A) having a diameter that is one half of the diameter of doublets 110 and 112.

In this working example, the diameters are 6.0 millimeters for the doublets 110 and 112, and 3.0 millimeters for the ball lenses 114 and 116. The image diameters are 1.5 millimeters.

The system 100 is designed so that all parts of each left/right image are mapped to within a selected distance of each other such that stereoscopic image quality is maintained. For video applications, this selected distance is typically a fraction of a video pixel. This is a difficult condition to satisfy, because the object-to-image ray paths through the lens system are quite different for the left and right image points of a common object point. The ray paths shown in FIG. 2 demonstrate how differently an object point is imaged through the lens elements for the left and right images.

The objective system 100 depicted in FIGS. 2 and 3 is able to map all parts of each left/right image to within a fraction of a video pixel to each other, because the large collimator doublets present equal-angle pairs from symmetrically disposed object points to the small ball lenses 114, 116. This exact equal-angle solution results in an accurate object/image mapping onto the final stereo image pair.

The accuracy and minimized distortion of the system of Table A is shown in the respective ray intercept curves shown in FIGS. 4A–4D. In each of those figures, for an identified object point the ray intercepts are shown as a function of relative aperture height.

Objective system 100, as described in Table A and shown in FIGS. 2 and 3, achieves accurate object/image mapping with simpler and fewer components than those used in prior art devices. Doublets 110 and 112 are relatively easy to manufacture compared to those used in prior art systems because they do not have any highly curved surfaces, nor do they have any curved surfaces that are nearly planer. Further, lenses 114 and 116 are identical and are made from widely available ball or spherical lenses.

As indicated in FIG. 1, the endoscope objective system 100 can be utilized in connection with optical fiber elements or a set of relay lenses 150, an example of which is described in the above-referenced U.S. Pat. No. 5,122,650.

Alternatively, an endoscope constructed in accordance with the invention can employ a conventional CCD array mounted within the same housing as the objective system. The CCD array can include left and right sensing elements 152, 154, disposed to receive the optical images generated at the output of ball lenses 114, 116 i.e. at surface 12. The design and construction of CCD elements having more than one photosensitive region in a monolithic package is well known in the art. The electrical signals generated by the CCD array can be conducted from the housing by a conventional conduit. This configuration eliminates the requirement for a relay lens system or optical fibers.

The system 100 depicted in FIGS. 2 and 3 offers advantages for use in medical endoscopes and industrial borescopes. The configuration offers the advantage of being adaptable to fit into a small tube diameter, as small as 2 millimeters. The design also affords high resolution and low distortion for diagnostic and surgical use, and for high-accuracy industrial measurement applications. The design is also relatively easy and inexpensive to produce.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Having described the invention, what is claimed as new and secured by Letters Patent is:

1. A stereoscopic objective lens system for a stereo video endoscope, the objective lens system converting light propagated from an object and received at an objective end of the objective system to pixel-mapped left and right optical images of said object at an image plane end of the objective system, the objective lens system comprising:

A. a first collimator doublet lens element proximate to the objective end for collecting light from points on the object, said first doublet lens having a first optical axis, a selected diameter and a selected optical power, B. a second collimator doublet lens for collecting light from said first collimator doublet lens, said second collimator doublet lens being disposed adjacent to said first collimator doublet lens and having an optical axis substantially collinear with the optical axis of the first collimator doublet lens, said second collimator doublet lens having a selected diameter and a selected optical power, whereby said first and second collimator doublet lenses cooperate to image the object points substantially to infinity so that light transmitted by the second collimator doublet lens from the object points is substantially collimated, C. a right/left stereo lens pair, said pair including a right ball lens and a left ball lens, said right and left ball lenses being adjacent to said second collimator doublet lens and disposed for collecting light from said second collimator doublet lens, said right ball lens and said left ball lens each having a respective optical axis substantially parallel to the optical axis of the second collimator doublet lens, wherein said first and second collimator doublet lenses and said right/left stereo lens pair cooperate so that the first and second collimator doublet lenses present equal-angle light ray pairs from symmetrically disposed object points to the ball lenses of said right/left stereo lens pair, whereby said right ball lens generates a right image at the image plane, and said left ball lens generates a left image at the image plane, such that corresponding portions of each right/left image are mapped to within a selected distance of each other.

2. A lens system according to claim 1 wherein the diameter of said second collimator doublet lens is approximately equal to the diameter of said first collimator doublet lens.

3. A lens system according to claim 2 wherein said right ball lens is substantially identical to said left ball lens.

4. A lens system according to claim 3 wherein said left ball lens and said right ball lens each have a circular cross-section transverse to the respective optical axes of said right ball lens and said left ball lens.

5. A lens system according to claim 3 wherein the diameters of said right ball lens and said left ball lens are substantially equal to one-half the diameter of said first and second collimator doublet lenses, and said optical axes of said right ball lens and said left ball lens are off-set from said optical axis of said first and second collimator doublet lenses by one-fourth the diameter of said first and second collimator doublet lenses.

6. A lens system according to claim 5 wherein said left ball lens and said right ball lens each have a circular cross-section transverse to the respective optical axes of said right ball lens and said left ball lens.

7. A stereoscopic objective lens system for a stereo video endoscope, the objective lens system converting light propagated from an object and received at an objective end of the objective system to pixel-mapped left and right optical images at an image plane end of the objective system, the objective lens system comprising:

A. a collimator lens system proximate to the objective end for collecting light propagated from points on the object, said collimator lens system having a defined optical axis, a selected diameter and a selected optical power, whereby said collimator lens system images the object points substantially to infinity so that light transmitted by said collimator lens system from the object points is substantially collimated, B. a right/left stereo lens pair, said pair including a right ball lens and a left ball lens, said right and left ball lenses being adjacent to said collimator lens system and disposed for collecting light from said collimator lens system, said right ball lens and said left ball lens each having a respective optical axis substantially parallel to the optical axis of the collimator lens system, wherein said collimator lens system and said right/left stereo lens pair cooperate so that the collimator lens system presents equal-angle light ray pairs from symmetrically disposed object points to the ball lenses of said right/left stereo lens pair, whereby said right ball lens generates a right image at the image plane, and said left ball lens generates a left image at the image plane, such that corresponding portions of each right/left image are mapped to within a selected distance of each other.

8. A lens system according to claim 7 wherein said collimator lens system comprises a first collimator doublet lens and a second collimator doublet lens, the diameter of said second collimator doublet lens being approximately equal to the diameter of said first collimator doublet lens.

9. A lens system according to claim 8 wherein said right ball lens is substantially identical to said left ball lens.

10. A lens system according to claim 9 wherein said left ball lens and said right ball lens each have a circular cross-section transverse to the respective optical axes of said right ball lens and said left ball lens.

11. A lens system according to claim 8 wherein the diameters of said right ball lens and said left ball lens are substantially equal to one-half the diameter of said first and second collimator doublet lenses, and said optical axes of said right ball lens and said left ball lens are off-set from said optical axis of said first and second collimator doublet lenses by one-fourth the diameter of said first and second collimator doublet lenses.

12. A lens system according to claim 11 wherein said left ball lens and said right ball lens each have a circular cross-section transverse to the respective optical axes of said right ball lens and said left ball lens.

* * * * *